United States Patent [19]
Murakami et al.

[11] Patent Number: 5,402,668
[45] Date of Patent: Apr. 4, 1995

[54] HIGH-RESOLUTION BEER VOLATILE ANALYSIS METHOD

[75] Inventors: Aki A. Murakami, Mequon; Henry Goldstein, Brookfield, both of Wis.

[73] Assignee: Miller Brewing Company, Milwaukee, Wis.

[21] Appl. No.: 193,664

[22] Filed: Feb. 8, 1994

Related U.S. Application Data

[63] Continuation of Ser. No. 980,827, Nov. 24, 1992, abandoned.

[51] Int. Cl.$^6$ ............................................. G01N 33/00
[52] U.S. Cl. .................. 73/19.02; 73/19.06; 73/23.42; 95/87; 96/104; 436/161
[58] Field of Search ................ 73/19.02, 19.06, 23.35, 73/23.42; 436/161, 177; 422/89; 95/87; 96/104

[56] References Cited
U.S. PATENT DOCUMENTS

| | | | |
|---|---|---|---|
| 3,205,700 | 9/1965 | Lively et al. | 73/19.02 |
| 3,673,853 | 7/1972 | Griswold et al. | 73/64.45 |
| 4,003,257 | 1/1977 | Fletcher et al. | 73/19.02 |

OTHER PUBLICATIONS

Paper entitled "Development of a High-Resolution Beer Headspace Analysis Method" by Aki Murakami et al., 1986, pp. 33-37.
Paper entitled "Trapping Efficiency of Capillary Cold Traps" by Anders Hagman et al., 1988, pp. 117-126.
Parts I and II of a paper entitled "Dynamic Headspace Gas Chromatography: Concentration of Volatile Components After Thermal Desorption By Intermediate CryofocusingIn a Cold Trap" by Peter Werkhoff et al., 1987, pp. 99-106.
Paper entitled "On-Column Cryogenic Trapping of Sorbed Organics for Determination by Capillary Gas Chromatography" by David Kalman et al., 1980.
Paper entitled "Efficiency of Cryogenic On-column and Pre-column Focusing of Volatile Compounds for High-Resolution GC" by S. Adam, 1983 pp. 36-37.
Paper entitled "Effects of Trapping Temperature and Film Thickness in Purge and Trap With Whole Column Cryotrapping on Fused Silica Columns" by J. F. Pankow, 1986, pp. 18-29.
Paper entitled "Cold Trapping of Volatile Organic Compounds on Fused Silica Capillary Columns" by J. F. Pankow, 1983, pp. 292-299.
Paper entitled "Rapid Analysis of Volatile Compounds in Food Products By Purge-And-Cold-Trapping-/Capillary Gas Chromatography" by H. I. Badings et al., May, 1984, pp. 523-532.
Paper entitled "Cryofocusing in the Combination of Gas Chromatography With Equilibrium Headspace Sampling" by B. Kolb et al., 1986, pp. 305-311.
Paper entitled "Determining Volatile Organics at Microgram-per-Litre Levels By Gas Chromatography" T. A. Bellar et al., Dec., 1974.
Paper entitled "Gas Chromatographic Analysis of Beer Flavor Compounds" by Ernest C. H. Chen, Ph.D., Nov., 1985.

(List continued on next page.)

*Primary Examiner*—James C. Housel
*Assistant Examiner*—Laura E. Collins
*Attorney, Agent, or Firm*—Quarles & Brady

[57] ABSTRACT

The invention is an apparatus and method for preparing volatiles collected from a sample for gas chromatographic analysis. Volatiles are collected from the sample in a volatile trap, such as a porous polymer trap. The volatile trap is then connected to a transfer line. The trap is heated to thermally desorb the volatiles, and an inert gas, such as helium, flows through the heated trap to transport volatiles through the transfer line into a capillary column located in a gas chromatograph oven. Inside of the oven, a portion of the capillary column is cooled with a cooling fluid such as liquid nitrogen to form a cold trap. When the cold trap is cooled, the desorbed volatiles are trapped in the cold trap. Then the cold trap is heated to allow the volatiles to be released and the volatiles are carried to the remainder of the capillary column for chromatographic analysis by an inert carrier gas.

5 Claims, 4 Drawing Sheets

OTHER PUBLICATIONS

*Proceedings American Society of Brewing Chemists,* "Comparison of Gas Chromatographic Methods For Analysis of Beer Flavors" by R. C. Lindsay et al., 1972, pp. 4–7.

*Journal of Chromatography,* "Pre-Concentration of Headspace Volatiles For Trace Organic Analysis By Gas Chromatography" by Alberto J. Nunez et al., 1984, pp. 127–162.

Symposium paper entitled "Measurement of Organic Pollutants in Water and Wastewater" Jun. 1978, pp. 108–129.

Paper entitled "Automatic System for Rapid Analysis of Volatile Compounds by Purge-and-Cold-Trapping-/Capillary Gas Chromatography" by H. T. Badings et al, Nov. 1985, pp. 755–763.

Article from *Journal of Chromatography* entitled "Quantitative Trapping and Thermal Desorption of Volatiles Using Fused–Silica Open Tubular Capillary Traps" by B. V. Burger et al., 1986, pp. 449–464.

Paper entitled "Cryogenic Techniques in Gas Chromatography, Part Two: Cryofocusing and Cryogenic Trapping": by Thomas A. Brettell et al., Nov. 1985, pp. 51–68.

Paper entitled "The Analysis of Volatile Compounds by Purge and Trap With Whole Column Cryotrapping (WCC) on a Fused Silica Capillary Column" by J. F. Pankow et al., Sep. 1984, pp. 504–508.

Paper entitled "Modifications of a Commercial Thermodesorption Unit to Obtain More Efficient Cryotrapping and Compatibility With a Mass Selective Detector (HP–5970)" by N. Schmidbauer et al., Jul. 1987, pp. 398–400.

Article from *ASBC Journal* entitled "Analysis of Volatile Beer Flavor Compounds by a Dynamic Headspace Entrainment Technique" by E. C. H. Chen, 1983, pp. 28–31.

HIGH-RESOLUTION BEER VOLATILE ANALYSIS METHOD

This application is a continuation of application Ser. No. 07/980,827, filed Nov. 24, 1992, now abandoned.

FIELD OF THE INVENTION

The present invention relates to the analysis of volatiles in an aqueous liquid using gas chromatography (GC). In a preferred aspect, the present invention relates, in particular, to beer volatile analysis.

BACKGROUND OF THE INVENTION

Beer volatile analysis relates to the analysis of volatiles dissolved in beer. Beer volatile analysis is sometimes referred to as beer headspace analysis, but will be referred to as beer volatile analysis herein. In volatile analysis, volatiles are isolated and typically analyzed in the gaseous phase using gas chromatography. There are other methods for determining the composition of the isolated volatiles (such as nondispersive infrared absorption, or laser techniques), but it is common to use gas chromatography. Volatile analysis can accurately identify the amount and types of volatile components in beer and, for this reason, it is useful for analyzing beer. In particular, volatile analysis is useful for testing beer flavor.

Because the concentration of volatiles in a sample are extremely low, the volatiles must typically be concentrated prior to chromatographic analysis. For volatile analysis to be accurate and sensitive, it is important to preserve the integrity of the volatiles as the volatiles are isolated, concentrated, and transported for chromatographic analysis. Heretofore, most volatile analysis systems have used "purge and trap" methods to isolate the volatiles from the beer (or other aqueous liquid). That is, a purging flow of pure helium gas is bubbled through beer and beer volatiles are trapped and concentrated on a porous polymer trap. The porous polymer trap is then transported to volatile analysis equipment where the trap is heated so that beer volatiles release or desorb from the trap. The desorbed beer volatiles are then carried into a gas chromatograph by flowing helium (or some other carrier gas) through the heated trap and into the gas chromatograph.

As mentioned above, the composition of the volatiles is usually measured using gas chromatography (GC). In capillary column gas chromatography, a sample of volatiles is injected into a capillary that has a thin film of methylsiloxane or some other liquid phase in which the different volatiles in the sample have different solubility. This is the primary mechanism for separating the compounds in the mixture. The capillary is then flushed with an inert carrier gas (e.g. helium) that transports the volatiles at different rates to a detector at the end of the capillary. Each volatile in the sample can be identified by its retention time in the capillary.

Capillary column gas chromatography is preferred over packed column gas chromatography because present capillary column GC can give better resolution than packed column GC. However, capillary columns allow only very small flow rates. This presents a problem because the desorption flow rate of helium needed to carry desorbed volatiles from a heated polymer trap into a capillary column is typically higher than that allowed through capillary columns. This problem is overcome in some systems by venting most of the helium gas that is carrying volatiles desorbed from the heated polymer trap to the atmosphere, and routing only a portion to the capillary column. In these systems, trace components are sometimes confused with base line noise in chromatographic data; or even lost entirely to the atmosphere.

FIGS. 1a and 1b show a prior art system where volatiles are transported from a heated polymer trap 15 to a cold trap 10 without venting a portion of the desorption helium gas to the atmosphere before cold trapping the volatiles in the cold trap 10 (see desorption/cold trapping mode shown in FIG. 1a). After volatiles are trapped in the cold trap 10, the cold trap 10 is heated and the volatiles are injected into a capillary column 21 located in a GC oven 14 by helium flowing at a relatively slow analysis flow rate (see injection mode shown in FIG. 1b).

In this prior art system, the cold trap 10 is within a capillary interface 12 located outside of a GC oven 14. The capillary interface 12 is a modified Model 1000 Capillary Interface Instrument (Tekmar, Inc., Cincinnati, Ohio) that is controlled electrically by a control unit 24. The cold trap 10 in the capillary interface 12 is a DB-1 fused silica capillary column (J&W Scientific, Inc., Folsom, Calif.) with a 0.32 mm I.D. that lies inside of a 1/16" O.D. stainless steel tube (not shown) in a liquid nitrogen reservoir (not shown). The cold trap 10 is about 5 cm in length.

Referring to FIG. 1a, a polymer trap 15, containing trapped beer volatiles, is connected to the capillary interface 12. Liquid nitrogen, supplied from a tank (not shown) is used to cool the cold trap 10 and a trap heater 16 heats the polymer trap 15 to desorb the beer volatiles from the polymer trap 15. Helium, supplied through desorption flow line 1, is then flowed through the system at a desorption flow rate which is relatively high. Desorbed beer volatiles are transported from the heated polymer trap 15 and are trapped in the cooled cold trap 10 and helium vents to the atmosphere 26. A maintenance flow 3 of helium is flowed into the capillary column 21 to maintain the integrity of the column 21.

Referring to FIG. 1b, after the volatiles are trapped in the cold trap 10, a valve 20 in the capillary interface 12 switches from a venting position to the GC capillary column 21. Then, the polymer trap 15 is removed, the carrier flow line 2 is attached to the interface 12, the cold trap 10 is heated rapidly, and helium is flowed through the system at the relatively slow analysis flow rate to inject the volatiles into the capillary column 21. The cold trap 10 can be heated rapidly because the stainless steel tubing (not shown) in the liquid nitrogen reservoir (not shown) acts as an electrical resistance heater. As the helium flow injects volatiles into thee capillary column 21, highly volatile compounds are retrapped at the head of the column 21 in the liquid phase until they are released by elevated GC oven temperatures.

In the prior art system shown in FIGS. 1a and 1b, some volatiles released from the heated polymer trap 15 might not be trapped in the cold trap 10 and, therefore, might flow out the vent 26 with the desorption flow of helium. Also, the integrity of volatile composition may be compromised by the time the volatiles are analyzed because of the several steps required to transport the volatiles to the GC column 21 (i.e. polymer trapping, desorption, cold trapping, heating, and retrapping in the liquid phase).

SUMMARY OF THE INVENTION

The present invention is a method and apparatus that can overcome the drawbacks of these prior art systems. It does this by cold trapping volatiles in a cold trap that is located inside a gas chromatograph oven. Volatile separation starts at the cold trap, which is an extension of the analytical column, as the GC oven heating program is started.

In one aspect, the present invention is a method for analyzing volatiles in a sample, such as, but not limited to, an aqueous liquid like beer. The method involves collecting volatiles in a volatile trap (preferably a porous polymer trap), heating the volatile trap to thermally desorb the volatiles, flowing inert carrier gas at a desorption flow rate through the heated volatile trap to transport desorbed volatiles into a capillary column located in a gas chromatograph oven, flowing a cooling fluid (preferably liquid nitrogen) over a portion of the capillary column to form a cold trap for trapping the desorbed volatiles transferred to the column, stopping the desorption flow of inert carrier gas through the heated volatile trap and stopping the flow of the cooling liquid through the cold trap when a sufficient amount of volatiles are trapped in the cold trap (preferably after at least two minutes and most preferably after four minutes), heating the cold trap to allow volatiles to be released to the remainder of the capillary column for analysis, and flowing inert carrier gas at an analysis flow rate through the cold trap to transport the released volatiles to fire remainder of the capillary column for analysis.

In another aspect, the present invention is an apparatus for preparing volatiles in sample for gas chromatography. Such an apparatus comprises a capillary column located in a gas chromatograph oven and a tube surrounding a portion of the capillary column so that a cooling fluid can be flowed over that portion of the capillary column to form a cold trap in the oven. The apparatus has a transfer line for flowing inert carrier gas to the capillary column. It also has a trap heater for heating a volatile trap to thermally desorb volatiles trapped in the volatile trap. Thermally desorbed volatiles can be transported from a heated volatile trap to a cooled cold trap by flowing inert carrier gas at a desorption flow rate through the heated volatile trap, through the transfer line, and into and through the cooled cold trap. Volatiles are transported from the cold trap to the remaining portion of the capillary column for gas chromatographic analysis by stopping the flow of cooling fluid and by flowing inert carrier gas at an analysis flow rate through the cold trap portion and into and through the remaining portion of the capillary column.

It is an object of the invention to provide an improved means for transporting volatiles from a sample to equipment for gas chromatographic analysis. More particularly, it is an object of the present invention to maintain the integrity of volatiles purged from a sample as they are transported to a gas chromatographic capillary column for analysis.

A related object of the present invention is to develop a system for using capillary column gas chromatography (because of its high resolution) to transfer the collected volatiles to a gas chromatographic column with very high efficiency using fewer steps. The present invention achieves this object because placement of the cold trap within the GC oven allows the cold trap to have a longer length, and therefore, virtually no desorbed volatiles can pass through the cold trap without being trapped. That is, virtually no desorbed volatiles are lost because the inert desorption flow of helium is void of volatiles when it vents to the atmosphere.

Also, because the cold trap is located within the GC oven and is an extension of the analytical column, chromatographic separation starts immediately, thus eliminating the retrapping of volatiles.

Other objects and advantages of the invention will become apparent upon reading the following detailed description and appended claims, and upon reference to the accompanying drawings.

BRIEF DESCRIPTION OF THE DRAWINGS

For a more complete understanding of this invention, reference should now be made to the embodiment illustrated in greater detail in the accompanying drawings (FIGS. 2-8) and described below by way of an example of the invention.

In the drawings.

DESCRIPTION OF PREFERRED EMBODIMENT

Figure 1A:
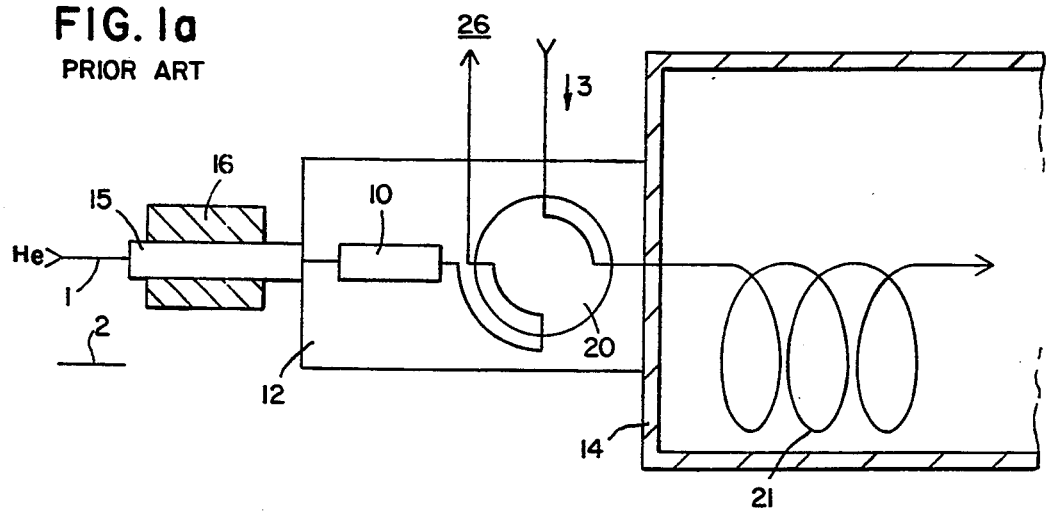
FIGS. 1a and 1b are schematic drawings showing the operation of a prior art system for transferring volatiles to a capillary column for gas chromatographic analysis.
Figure 1B:
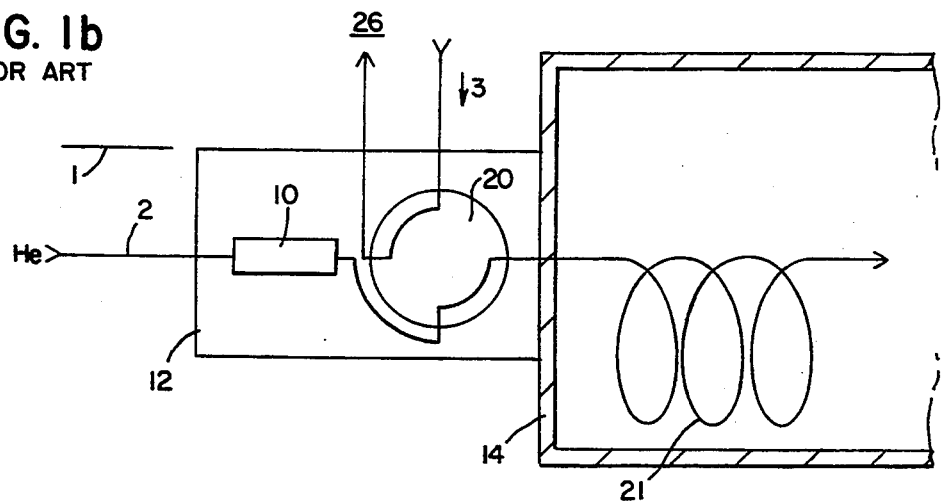
Figure 2A:
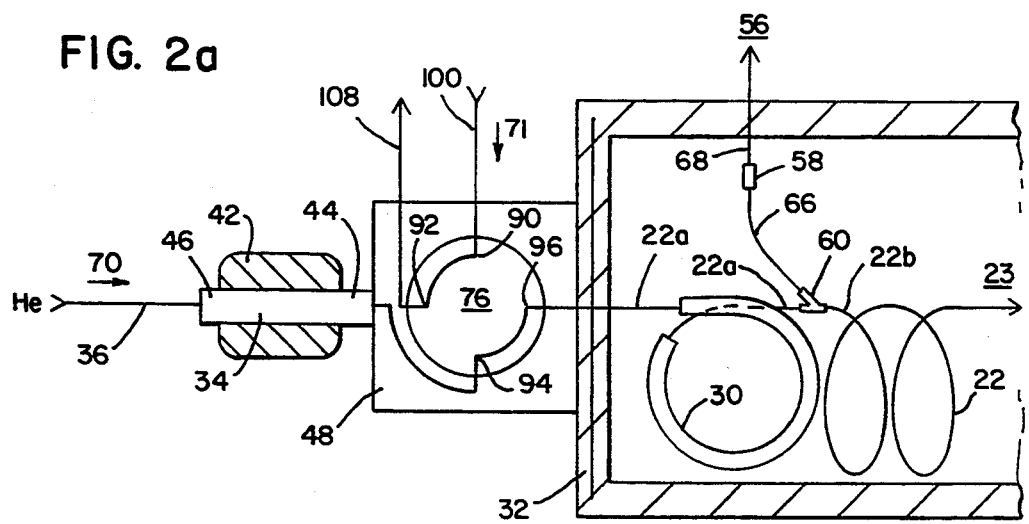
FIGS. 2a and 2b are schematic drawings showing the operation of the present invention in which volatiles are transferred to a capillary column for gas chromatographic analysis.
Figure 2B:
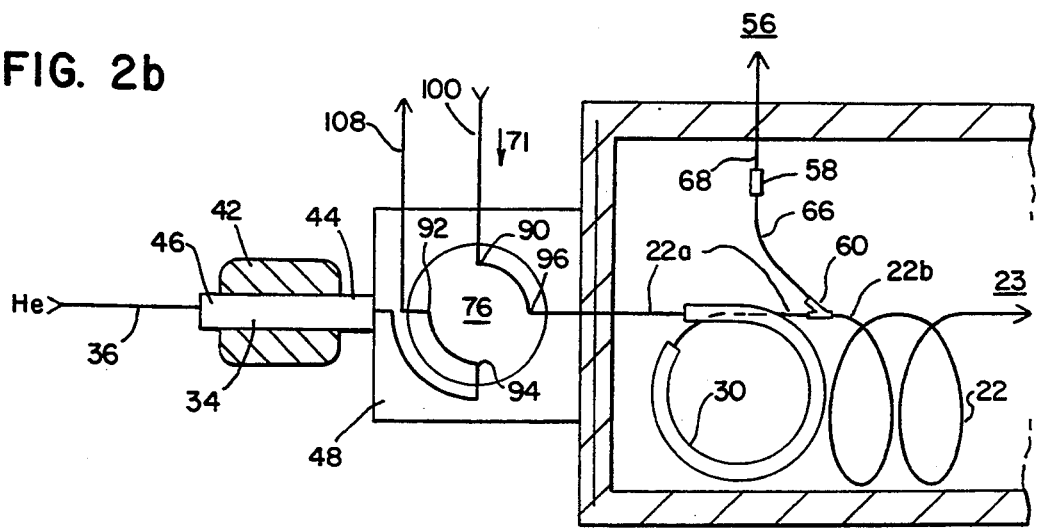

FIGS. 2a and 2b are schematic drawings of the system of the present invention. A general comparison of this system to the prior art system in FIGS. 1a and 1b, shows that the cold trap 30 in the present invention is located within the GC oven 32 (see FIG. 2a), rather than in the modified capillary interface 12 that is external to the GC oven 14 (see FIG. 1a). Another difference is that the cold trap 30 in the present invention (FIG. 2a) can be longer (i.e. 137 cm versus 5 cm) than the cold trap 10 of the prior art system (FIG. 1a). This feature ensures that virtually no volatiles are vented to the atmosphere before analysis.

In the present invention, chromatographic analysis can start immediately after stopping the flow of liquid nitrogen to the cold trap 30 and starting a GC oven 32 temperature program, since the beer volatiles are, at that point in time, at the head of the analytical column 22 (i.e. capillary column 22A to be exact) instead of in an external cold trap. In addition, highly volatile compounds are not "retrapped" in the liquid phase at the head of the column. It is believed that this feature preserves the integrity of beer volatiles better than the prior art.

In order to facilitate the transportation of volatiles from a heated polymer reap 34 to the cold trap 30 located in the GC oven 32, it is preferred in the present invention to use a heated interface box 48. The box 48 is heated with a valve heater 114 (see FIG. 6) controlled by variable voltage transformers (not shown). Besides heating the interface box 48, a cartridge heater 128 heats a transfer line 130 through which desorbed volatiles are transported from the interface box 48 through a wall 132 of the GC oven 32 (see FIG. 7). These two features, a heated interface box 48 and a heated transfer line 130, help preserve the integrity of desorbed beer volatiles as they are transported to the cold trap 30 located in the GC oven 32.

Turning now to the details of the preferred embodiment of the present invention, beer volatiles are collected in the porous polymer trap 34 by purging refrigerated beer in a 500 ml gas washing bottle for 5 minutes with helium. No anti-foam is added to the beer and this beer is stirred gently during the purging process. Larger vessels (1 or 4 liters) can be used to collect larger volumes of volatiles. Teflon tubing and fittings are used to connect the washing bottle to the porous polymer trap 34 and to a purging helium gas line (not shown). The polymer traps 34 are made of Pyrex glass tubing (7.5 cm, 6 mm O.D., 2 mm I.D.) packed with porous polymer of 60/80 mesh (2, 6-diphenyl-p-phenylene oxide). The porous polymer is held in place with silanized glass wool plugs. Before use, the polymer trap 34 is conditioned at 280° C. with helium gas flow.

The purging flow of helium to the washing bottle for purging the volatiles from the beer is preferably controlled by an electronic flow controller (not shown) at a rate of 40 ml per minute. (E.g. Matheson Model 8274 with a Model 8272-042 transducer; 50-70 psi inlet, 0-20 psi outlet.) A mechanical type flow controller is more difficult to use because of carbon dioxide from the beer.

Figure 3A:
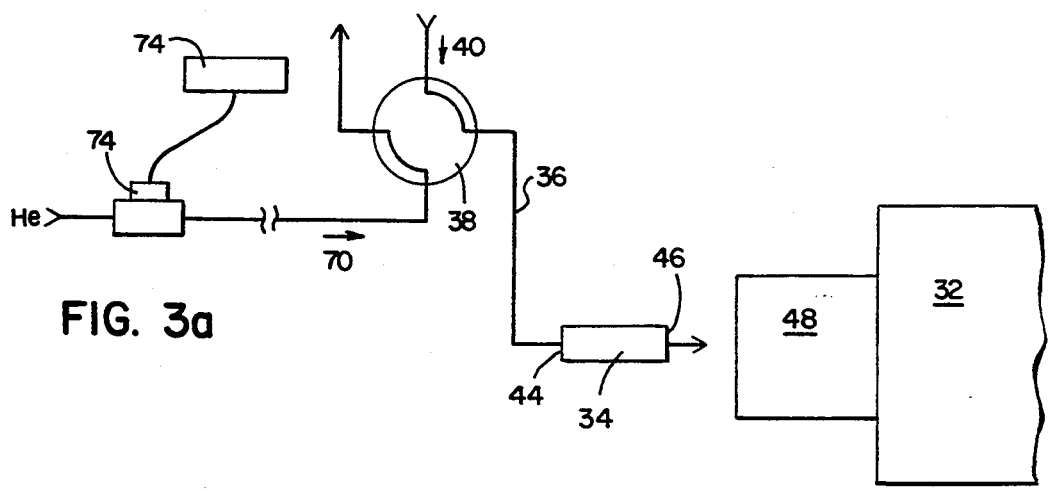
FIGS. 3a and 3b are schematic drawings showing the operation of a conditioning/desorption flow switch in the preferred embodiment of the apparatus of the present invention.

Referring to FIG. 3a, after volatiles are purged from the beer for five minutes and trapped in the polymer trap 34, the trap 34 is connected to line 36 leaving a four-way valve 38. A conditioning flow 40 of helium flows into the four-way valve 38 and out line 36 passing through the trap 34 to remove water and ethanol from the trap 34. It is preferred to condition the polymer trap 34 for 20 minutes with helium flowing at 20 ml/minute.

Referring to FIG. 3b and again to FIG. 2a, after water and ethanol are removed by conditioning the polymer trap 34, the trap 34 is reversed in line 36 and a trap heater 42 is placed over the trap 34. An end 44 of the trap 34 opposite from an end 46 (now connected to line 36) is connected to an interface box 48. Thumb nuts (e.g. Envirochem UX-08-3005) can be used to make all of the trap 34 connections.

Figure 4:
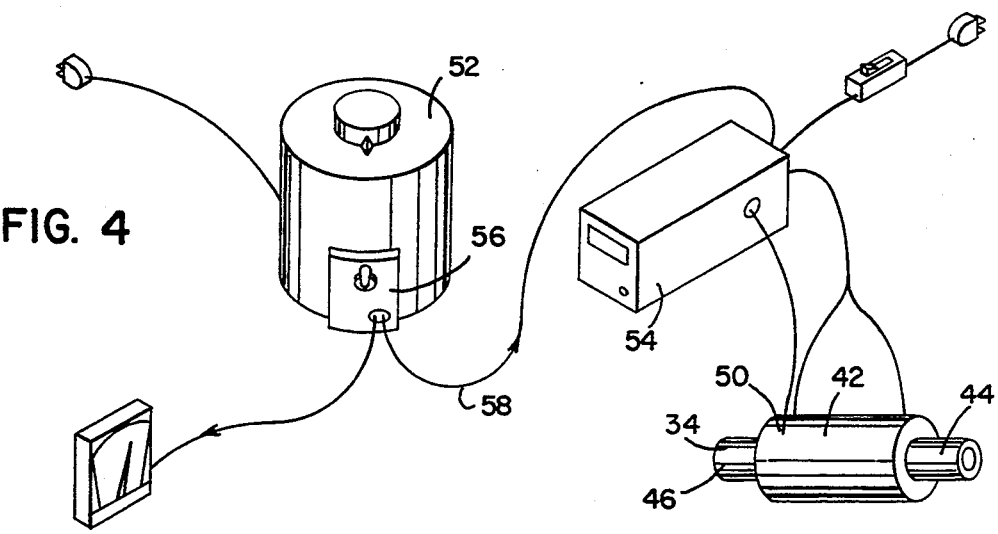
FIG. 4 is a schematic drawing of a system for heating a polymer trap used in the preferred embodiment of the apparatus of the present invention.

Referring to FIG. 4, the trap heater 42 is made of 20 gauge nichrome wire (Pelican, Inc, Naples, Fla.) wound over a cylindrical mold of a trap 34 tubing made from a high temperature cement. The trap heater 42 is made by coating the nichrome wire with the high temperature cement. A thermocouple 50 is attached to the cement coating and another coat of high temperature cement is applied to the heater 42. If necessary, a third coating of high temperature cement can be applied. The cylindrical mold (4 cm × 1.5 cm diameter) is constructed by coating the high temperature cement on a dummy polymer trap wrapped with a piece of aluminum foil. The foil prevents permanent adhesion of the cement when dried to the dummy polymer trap and allows the dummy trap to be easily removed. (Thin coats of cement are used to avoid cracking.)

The heater 42 is connected to a variable transformer 52 (Powerstat LW136BT, Superior Electric Company) and to a digital temperature controller 54 (Omega CN5000). Both the temperature controller 54 and the variable transformer 52 receive power from conventional AC power sources (i.e. 120 volts, 60 hertz). The transformer 52 has a switch 56. When the switch 56 is in the "on" position, electric power (0–30 AC volts, 0–25 amps) flows to the temperature controller 54. The temperature controller 54 receives a signal indicating the temperature of the heater 42 from the thermocouple 50 which is electrically connected to the temperature controller 54. Based on the temperature of the trap 34, the temperature controller 54 regulates the amount of power flowing from the transformer 52 to the 20 gauge nichrome wire coil 42. Different transformer 52 voltage settings may be required for heaters 42 that use different amounts of nichrome wire. Also, it is important to note that each heater 42 should be calibrated in connection with the thermocouple 50 and the actual temperature measured inside of the heater 42 that transfers to the trap 34.

Referring to FIG. 2a, desorption should be as efficient as possible to transfer volatiles completely from the heated polymer trap 34 to the cold trap 30. This is an important factor for recovering volatiles for analysis. For efficient transfer of volatiles, a reasonably fast desorption flow rate is preferred to avoid a long desorption period that can cause thermal degradation of volatiles and peak width broadening. To be able to use a 22 ml per minute desorption flow rate, a vent 56 is installed between the capillary column 22A going through the cold trap 30 and the analytical portion 22B of the capillary column 22. The vent 56 is closed during chromatographic separation. If the vent 56 is not opened during desorption, the desorption flow rate is greatly reduced preventing the transfer of volatiles from the porous polymer trap 34 to the cold trap 30. Also, in the vented mode, a normal desorption flow rate of 22 ml/minute produces better results than a slower desorption flow rate of 11 ml/minute.

The desorption trapping step begins by first opening the flow vent 56 located after the cold trap 30 in the GC oven 32. The flow vent 56 is opened by opening valve 58 that is located in line 66 after a flow splitter 60. The flow splitter 60 is located in the GC oven 32 after the capillary column 22A going through the cold trap 30 and splits flow exiting the capillary column 22A before entering the capillary column 22B. Because of the high back pressure caused by the capillary column 22B, almost all the flow will exit through the flow vent 56.

Figure 5:
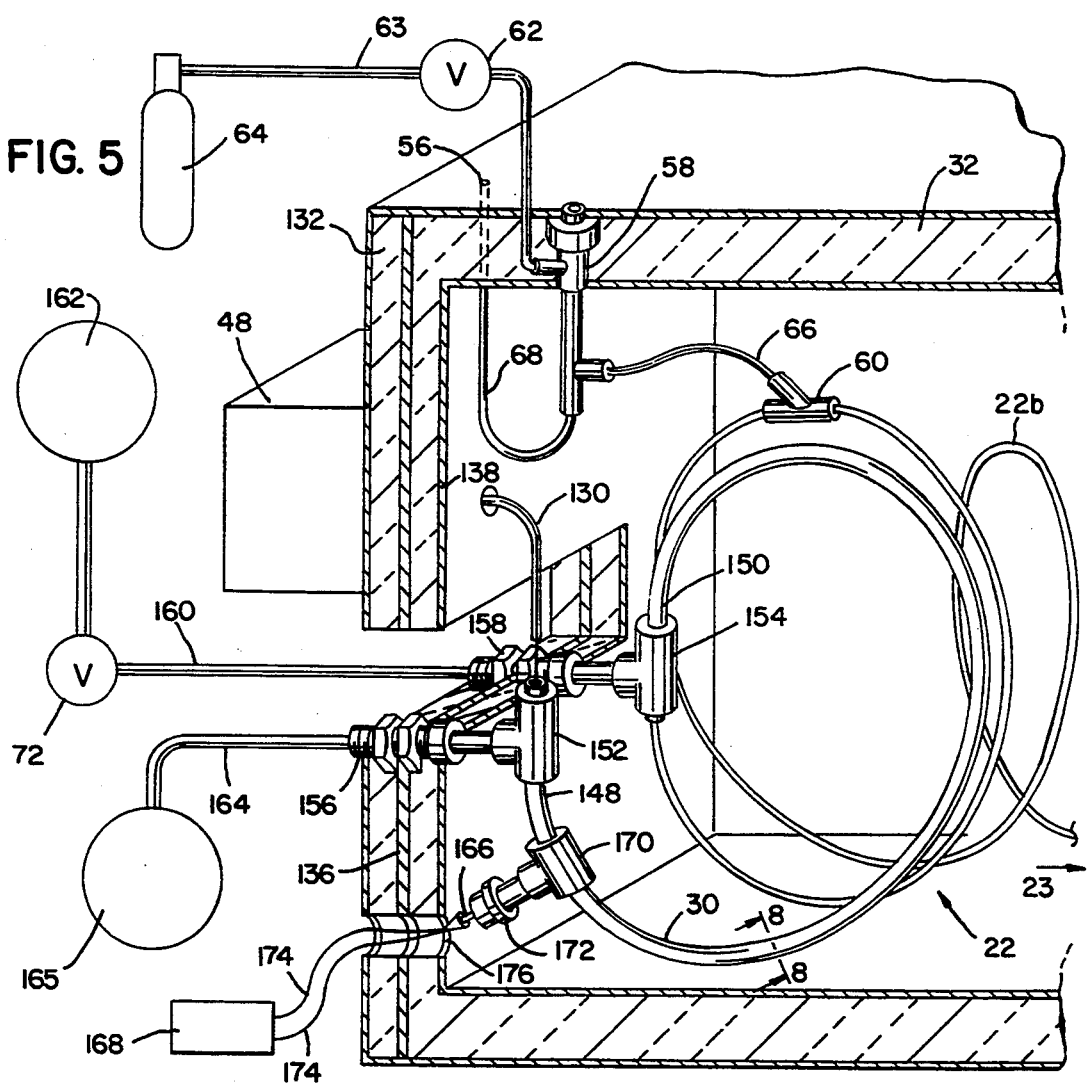
FIG. 5 are schematic drawings of the details of a cold trap and a vent in a preferred embodiment of the apparatus of the present invention.

The flow vent 56 apparatus is shown in detail in FIG. 5. The preferred flow splitter 60 is a low volume glass "Y" splitter (Chemical Research Supplies, Universal Y Connector 207960). Polyimide resin glue can be used to help prevent the connections between the flow splitter 60 and the capillary column 22 from becoming loose due to vibration.

The on/off valve 58 is activated by a pneumatic toggle valve 62. The valve 58 can be quickly opened and shut with the flick of a switch on the toggle valve 62. The valve 58 has a small dead volume and is rated up to 300° C. and 500 psi. This style of valve 58 is well suited for repeated on/off operation without the over tightening or loose closure that is possible with screw-type valves.

The pneumatic toggle valve 62 is connected to an air tank 64 with 60 psi output. A 1/16" stainless steel tube 63 conveys air from the air tank 64 to the toggle valve 62 and, if the toggle valve 62 is open, to the valve 58. When the toggle valve 62 is turned on and air flows to the valve 58, the valve 58 is opened and excess helium from splitter 60 and line 66 flows through line 68 and out vent 56 to the atmosphere. Line 68 is made of 1/16" stainless steel tubing.

When the flow vent 56 is opened, a liquid nitrogen valve 72 is also opened to cool the cold trap 30. The four-way valve 38 is switched from the conditioning flow of helium 40 to the desorption flow 70 (see FIG. 3a and 3b). And, the heater 42 is turned on to start the desorption/cold trapping process. The trap heater 42 is heated to a predetermined temperature (230° C.) in a short period of time and maintained at that temperature until it is turned off after the desorption/cold trapping step.

Figure 3B:
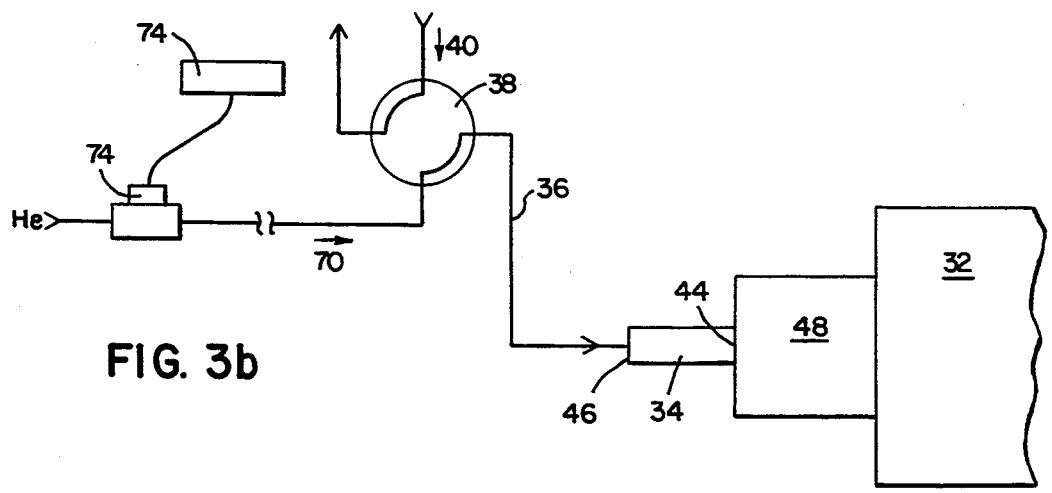

Referring to FIG. 3b, the desorption flow 70 is controlled by an electronic flow controller 74 (Matheson Model 8274 with Model 8272-0412 transducer, 100 psi inlet and 60 psi outlet rating). The flow controller 74 is set to maintain a constant flow with the back pressure from the cold trap/analytical column 22. Both the desorption 70 and conditioning 40 flows flow into the valve 38. The valve 38 allows quick and easy switching from the conditioning flow 40 to the desorption flow 70 without physically disconnecting and connecting lines when the required flow rates are needed. An ⅛" four-way switching valve (Valco 24 UWP) is an adequate valve 38.

When the four-way switch 38 is in the proper position, the desorption flow 70 flows at a desorption flow rate controlled by flow controller 74 through valve 38, through line 36 and through the heated polymer trap 34. The desorption flow 70 of helium then carries desorbed volatiles from the heated polymer trap 34 through the interface box 48 and into the cold trap 30 where the volatiles are trapped. The helium continues to flow through the cold trap 30 and most of it is vented to the atmosphere through vent 56.

Figure 6:
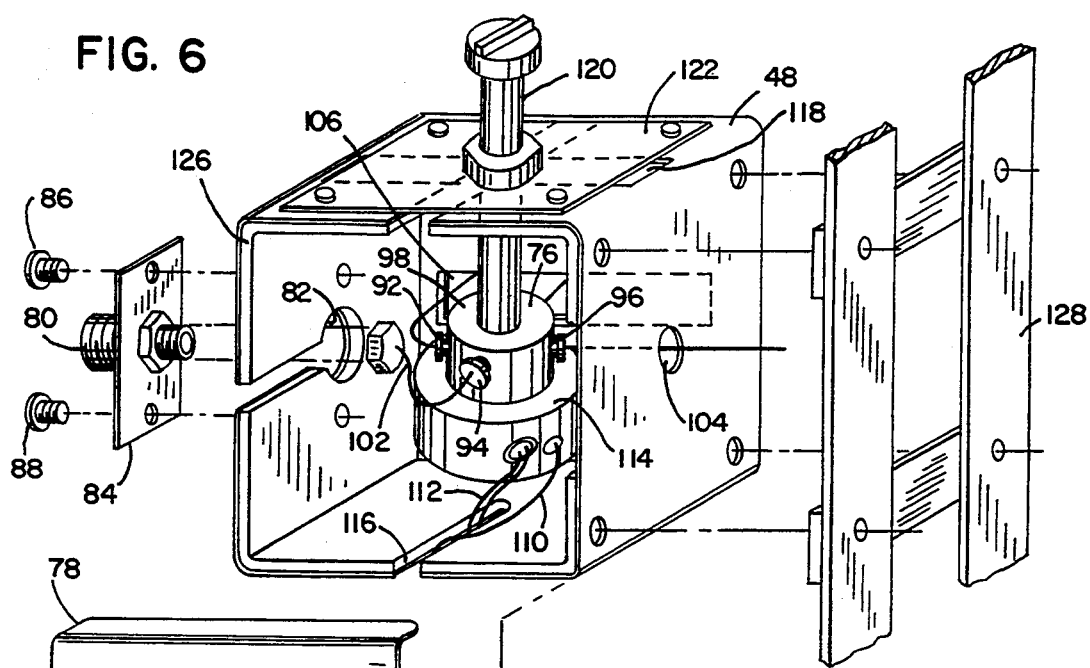
FIG. 6 is a schematic drawing of the details of an interface box in a preferred embodiment of the apparatus of the present invention.

The interface box 48 is shown in detail in FIG. 6. The interface box 48 is a modified heated valve enclosure (Valco Model HVE-18). A 1/16" four-way flow switching valve 76 (Valco Model 6C 4WT) is inside the interface box 48. The valve 76 can be set so that either the desorption flow 70 of helium (carrying desorbed volatiles) flows to the cold trap 30 or so that an analysis flow 71 of helium gas flows through the cold trap portion 30 of the capillary column 22A and carries volatiles released from the cold trap 30 to the remainder of the capillary column 22B for GC analysis. (See FIGS. 2a and 2b).

Referring again to FIG. 6, the interface box 48 has a lid 78 which is shown to be removed to the front of the box 48. A fitting 80 to allow connection to the polymer trap 34 is secured into an opening 82 in the box 48. The fitting 80 is attached to the box 48 with torque plates (only one shown) 84 and two screws 86 and 88. The fitting 80 is a ¼" to 1/16" stainless steel Swagelok union. The torque plates 84 anchor the fitting 80 to the interface box 48 firmly. This prevents twisting from repeated attachment and detachment of the polymer trap 34. Self clinching nuts can be used so that the plate holding screws 86 and 88 can be directly fastened to the box 48.

Referring again to FIGS. 2a and 2b, the four-way valve 76 in the interface box 48 has four ports 90, 92, 94 and 96. Each of these ports is located at a position 90° from two circumjacent ports along the circumference of a round valve body 98 (see FIG. 6). In FIG. 2, it can be seen that the desorption flow 70 of helium enters through port 94 and leaves from port 96 when the system is in a desorption/cold trapping mode or from port 92 when the system is in the analysis mode. The analysis flow 71 of helium flows through line 100 and enters the valve 76 through port 90 and leaves from port 92 when the system is in a desorption/cold trapping mode and from port 96 when the system is in an analysis mode.

Referring again to FIG. 6, the fitting 80 (for the polymer trap 34 attachment) connects to a stainless steel tube 102 inside the interface box 48. The stainless steel tube 102 is coated inside with fused silica (Restek Silcosteel 1/16" O.D., 0.03" I.D., 17.9 cm). The other end of the silica coated stainless steel tube 102 connects to port 94 on the valve 76. Fused silica tubing or silica coated tubing is well suited for the transfer of volatiles. The silica coated stainless steel tube 102 can be bent more easily than pure fused silica tubing.

A circular opening 104 in the interface box 48 allows the port 96 to be connected to the cold trap 30 and the capillary column 22A. A rectangular opening 106 on the rear face of the interface box 48 (as shown in FIG. 6) allows the analysis flow 71 of helium through line 100 to be connected to port 90 (not shown in FIG. 6). The rectangular opening 106 also allows the vent line 108 connected to port 92 to travel outside the box 48. A thermocouple 110 enters through the rectangular opening 116. Thermocouple 110 monitors the temperature of the valve heater 114 and is connected to a thermometer (not shown). The valve heater 114 is powered by a variable transformer (not shown). As discussed above, the interface box 48 is heated so that during the desorption/cold trapping process the integrity of beer volatiles flowing from the heated polymer trap 34 to the cold trap 30 does not degrade.

Heater 114 in the interface box 48 is set at a normal of 130° C. and experiments have shown that it cart be raised to 185° C. without changing the accuracy of the system.

A power cord 112 for the valve heater 114 located under the valve 76 enters through a slit 116 on the bottom of the box 48.

A cross-shaped opening 118 in the top of the interface box 48 allows the valve 76 to be moved during installation and maintenance. A stem 120 for valve 76 exits the box 48 top through the cross-shaped opening 118. The valve stem 120 is anchored to the top of the box 48 by an anchor plate 122 that is screwed to the box 48 top after the valve 76 is properly positioned. The anchor plate 122 can be unscrewed and the valve 76 can be moved to allow access to a column connecting nut 124 (not shown) to ease attachment of the capillary column 22A which goes through a heated transfer line 130 (leading to the cold trap 30—see FIG. 7) to port 96. For instance, unscrewing the anchor plate 122 allows movement of the valve 76 without letting the valve 76 drop into the interface box 48.

Insulation 126 is placed along the inside walls of the interface box 48. Preferably, the insulation 126 is ceramic fiber board fitted to match the openings 82, 104, 106, 118, and 116 of the interface box 48. The insulation 126 is preferably coated with a coating cement to prevent spalling. (Fiberfrax Coating Cement, QF-180, Carborundum Company.) Coated insulation 126 has a cast like finish and is easy to install and remove. More insulation can be used in the box 48 where desired.

The interface box 48 is mounted on a bracket 128 that is on the side of the GC oven.

Figure 7:
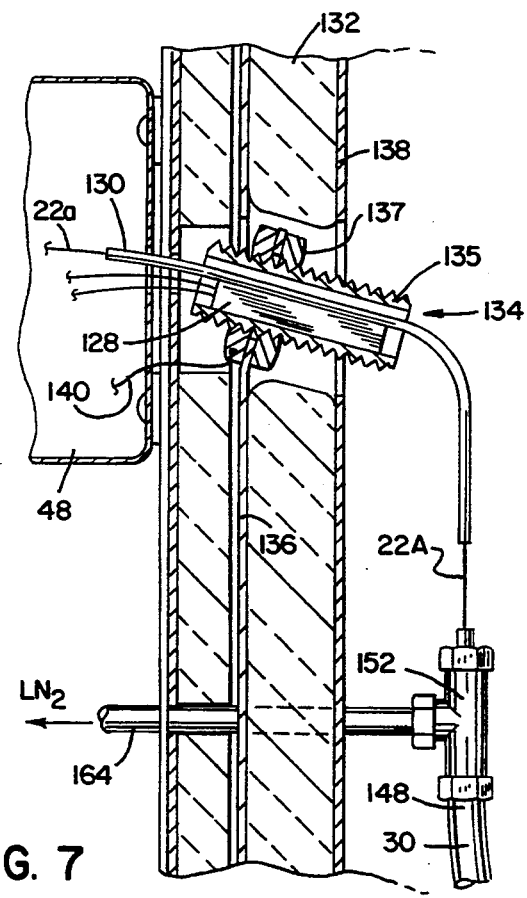
FIG. 7 is a schematic drawing of a heated transfer line in the preferred embodiment of the apparatus of the present invention.

Referring to FIG. 7, a portion 134 of the capillary column 22A, referred to herein as a transfer line 134, is also heated. The capillary column 22A attaches on one end to valve 76, runs through wall 132 of the GC oven 32 and leads to the cold trap 30 inside the GC oven 32. The capillary column 22 is continuous from the point where it attaches to the valve 76 through the cold trap 30 past the flow splitter 60 and through the remainder of the column 22B to the GC detector 23 (see FIG. 2). The part of the capillary column 22 for transporting volatiles in the transfer line 134 in the cold trap 30 (i.e. from port 96 on valve 76 to flow splitter 60) is designated as 22A, and is referred to herein as the transfer line/cold trap portion 22A of the capillary column 22. The transfer line/cold trap portion 22A of the capillary column 22 is preferably a DB-1 fused silica column with a 0.32 mm I.D. and a 0.25 mm film (i.e. wide bore). The portion of the capillary column 22 after the flow splitter 60 is designated as 22B and is referred to as the analytical portion 22B of the capillary column. The analytical portion 22B is a 60 meter DB-1 fused silica column with an 0.25 mm I.D. and a 0.25 mm film (i.e. narrow bore).

Referring again to FIG. 7, the transfer line 134 is heated with a transfer line heater 128. The transfer line heater 128 is a cartridge heater (Hotwatt SC 122, 35W ⅜" O.D., 2" length). The temperature of the heated transfer line 134 is not critical as long as it is adequately heated so that the volatiles are adequately transported to the cold trap 30. Experimentation has shown that 142° C. is a sufficient temperature and that higher temperatures do not improve the operation of the system. A thermocouple 140 monitors the temperature of the transfer line body 135 and the heater 128 is powered by a variable voltage transformer. The transfer line body 135 is firmly attached to a metal sheet 136 using a nut 137 that is placed inside the wall 132 of the GC oven 32. The transfer line body 135 is a ¼" Swagelok bored-through bulkhead union. A 1/16" stainless steel guide tube 130 is inserted through the union 135 with the heater 128. The stainless steel tube 130 helps conduct heat from the heater 128 to the heated capillary column before the cold trap 30 which would otherwise not be heated.

Figure 8:
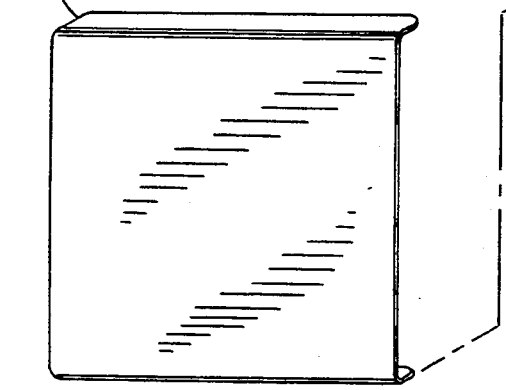
FIG. 8 is a cross-sectional view of the cold trap of the preferred embodiment of the apparatus of the present invention.
Figure 8:
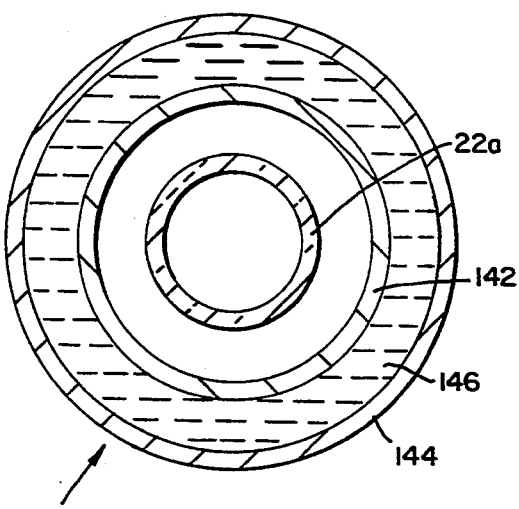

The configuration of the cold trap 30 in the GC oven 32 can be seen in FIG. 5. Generally speaking, the cold trap 30 is a single coil of a stainless steel tube 142 in a copper tube 144 wherein liquid nitrogen flows between the stainless steel tube 142 and the copper tube 144 (see FIG. 8). Referring to FIG. 8 which shows a cross section of the cold trap 30, the cold trap portion of the capillary column 22A is located inside of a 1/16" stainless steel tube 142. The stainless steel tube 142 has an 0.040" I.D. The tube 142 with the capillary 22A inside of it is located inside of a copper outer tube 144 having a ¼" O.D. Liquid nitrogen 146 flows between the stainless steel tube 142 and copper tube 144 to cool the capillary 22A.

Referring again to FIG. 5, the cold trap 30 is approximately 137 cm long and configured in a single coil having about a 22 cm diameter. The cold trap 30 is installed inside of the GC oven 32 by connecting the ends 148 and 150 of the cold trap 30 to the wall 132 of the GC oven 32 below the interface box 48. The ends 148 and 150 of the cold trap 30 are connected to the wall 132 using union tees 152 and 154 which are fastened to the wall 132 of the GC oven 32 using ¼" Swagelok bulkhead unions 156 and 158. Both the inlet 158 and the outlet 156 bulkhead unions protrude from the wall 132 underneath the interface box 48 so that connections to liquid nitrogen can be made from outside of the GC oven 32. Holes are cut through the metal sheets 136 and 138 in the wall 132 to mount the bulkhead unions 156 and 158.

Insulated tubing 160 from the inlet bulkhead union 158 connects to a liquid nitrogen tank 162. Valve 72 (Nupro Bellows Valve N-4BKT) in line 160 controls the flow of liquid nitrogen into the cold trap 30.

An insulated ¼" tube 164 is attached to the outlet bulkhead union 156 and leads to a container 165 in which spent liquid nitrogen is reclaimed. A ¼" phase separator is installed at the end of tube 164.

The liquid nitrogen in the cold trap 30 flows in the opposite direction to the flow of helium gas (containing desorbed volatiles) passing through the inside of the capillary column 22A. This makes the cold trap 30 coldest at the end 150 towards the end of the analytical portion 22B (i.e. narrow bore) of the capillary column and warmest at the end 148 near the transfer line 130. This temperature gradient along the length of the trap 30 avoids sudden condensation of all the volatiles at the entrance (i.e. 148) of the cold trap 30. To further facilitate the avoidance of sudden condensation at the entrance of the cold trap 30, desorption can be started while the cold trap 30 is being cooled down when the temperature gradient is significant. Once the cold trap 30 reaches its lowest temperature and the temperature gradient along the cold trap 30 is insignificant, the majority of volatiles are already trapped.

The temperature of the cold trap 30 is monitored near the outlet end 148 of the cold trap 30 using a platinum resistant thermometer probe (RTD) 166 (Omega PR-11-2-100-1/8-2-E with 26 gauge 48" leads insulated with EXGG, range −200° to 600° C. The RTD 166 is connected to a digital thermometer 168 (Omega model 651-385 with a DS-651-385 case and power cord with a range from −200° to 850° C.) so that the temperature of the cold trap 30 can be displayed. The RTD 166 is installed in the cold trap 30 using a ¼" union tee 170 and a reducer fitting 172. Leads 174 from the RTD 166 pass through a hole 176 in the wall 132 to the thermometer 168.

Before cooling, the cold trap 30 is maintained in the GC oven 32 set at 40° C. At this temperature, the cold trap 30 can be cooled with a reasonable amount of liquid nitrogen within a reasonable amount of time. The liquid nitrogen valve 72 is opened to cool the cold trap 30. With the GC oven 32 set at 40° C., it takes 3–5 minutes with continuous liquid nitrogen flow to cool the cold trap to −185° C. It is preferred to leave the GC oven set at 40° C., rather than leaving the GC oven off because there is better reproducibility.

To begin the desorption/cold trapping process, the valve 76 is switched to the desorption/cold trapping position, the vent 56 is opened, and the desorption flow 70 is started by switching the flow valve 38. When the cold trap 30 reaches 0° C. the trap heater 34 is turned on. The trap heater 34 is heated in a relatively short period of time to a temperature of 230° C. The desorption flow of helium begins carrying desorbed volatiles to the cold trap 30 when the trap heater heats up. For a beer headspace volume collection of 200 ml (at room temperature) with the cold trap starting temperature at 0° C. and a polymer trap being heated to 230° C., it has been found that the time period for desorption/cold trapping should be between four and six minutes.

Referring to FIG. 2b, when the desorption/cold trapping process is over, the flow vent 56 is closed by closing valve 58. The valve 76 in the interface box 48 is switched so that an analysis flow 71 of helium gas flowing at a relatively slow analysis flow rate flows through the valve 76, into the cold trap 30, and through to the analytical portion 22B of the capillary column 22. The desorption flow 70 of helium now flows through the interface box 48 and is vented to the atmosphere through vent 108. The flow of liquid nitrogen to the cold trap is shut off at this point by closing valve 72. Contemporaneously, the GC oven 32 temperature program begins and chromatographic analysis starts. The trap heater 42 can be left on for about 10 to 15 minutes while the helium flow 70, which is now venting to the atmosphere, conditions the trap 34.

A Hewlett Packard Model 5880A gas chromatograph is used. A flame ionization detector 23 (FID) is used to monitor the volatiles exiting the analytic portion 22B of the capillary column. A flame photometric detector (FPD) can be used to monitor sulfur compounds, or a mass spectrometer can be used for compound identification.

For chromatographic analysis of beer volatiles, the GC oven temperature program holds the temperature in the GC oven 32 at 40° C. for 4 minutes, raises the temperature at 2° C. per minute until the oven temperature is 132° C., and raises the temperature at 20° C. per minute until the oven temperature is 175° C. The oven remains at 175° C. for 15 minutes.

As the analysis flow 71 of helium flows through the cold trap 30, (now being heated by the elevated GC oven temperature because there is no longer a flow of liquid nitrogen to the cold trap 30), it carries volatiles separated in the analytical column 22B to the detector 23. The detector 23 measures the amount of volatiles carried to it. This measurement can then be recorded on a strip chart.

While the description of the preferred embodiment discusses how the present invention is useful for beer volatile analysis, the present invention is not limited to analyzing beer volatiles. Rather, the present invention may be used in any system that requires the transfer of volatiles into an analytical column 22 for gas analysis. The sample from which the volatiles originate need not even be a liquid. The present invention may be used in the analysis volatiles collected from any type of sample where the vapor pressure of the volatiles is sufficient so that the volatiles can escape from the sample, and thus be collected for analysis. The present invention is therefore not limited to analyzing volatiles from beer samples, but also includes the analysis of volatiles from other types of samples that have a vapor pressure, including, but not limited to, gases, liquids, solids, food products, biological samples, paints, coatings, resins, lubricants, paper good, woods, plastics, polymers, etc.

We claim:

1. A method for analyzing volatiles in a sample comprising steps of:
   collecting volatiles from a sample in a volatile trap;
   connecting the volatile trap to a transfer line after the volatiles are collected in the volatile trap;
   heating the volatile trap to thermally desorb the volatiles;
   flowing inert carrier gas at a desorption flow rate through the heated volatile trap to transport desorbed volatiles through the transfer line into a first portion of the capillary column located in a gas chromatograph oven, said gas chromatograph oven being preheated to a first temperature;
   flowing a cooling fluid over said first portion of the capillary column to form a cold trap for trapping the desorbed volatiles, the desorbed volatiles being transported into the cold trap while the cold trap decreases in temperature from the first temperature to a second temperature;
   venting excess inert carrier gas from the capillary column at an intermediate point after the inert carrier gas flows through the cold trap, which venting occurs when the inert carrier gas is flowing at the desorption flow rate and the cooling fluid is flowing over said first portion of the capillary column forming the cold trap;
   stopping the desorption flow of the inert carrier gas through the heated volatile trap and stopping the flow of the cooling fluid over the cold trap when a sufficient amount of volatiles are trapped in the cold trap;
   heating the cold trap to cause volatiles to be released into to a remainder of the capillary column; and
   flowing inert carrier gas at an analysis flow rate through the cold trap portion of the capillary column to transport released volatiles through the remainder of the capillary column and to a detector for gas chromatographic analysis.

2. The method as recited in claim 1 further comprising the step of conditioning the volatile trap with helium gas after the volatiles are collected in the volatile trap and before the volatile trap is heated to thermally desorb the volatiles.

3. The method as recited in claim 1 further comprising the step of maintaining the gas chromatograph oven at the first temperature when the cooling fluid flows over the first portion of the capillary column that forms the cold trap.

4. The method as recited in claim 1 wherein the cooling fluid is liquid nitrogen.

5. The method as recited in claim 1 wherein the step of heating the cold trap comprises allowing the temperature of the cold trap to increase to the first temperature produced by the gas chromatograph oven without using additional heating devices.

* * * * *